US009000199B2

(12) United States Patent
Hong et al.

(10) Patent No.: US 9,000,199 B2
(45) Date of Patent: Apr. 7, 2015

(54) POROUS CERAMIC MATRIX

(75) Inventors: Liang Hong, Singapore (SG); Xinwei Chen, Singapore (SG)

(73) Assignee: National University of Singapore, Singapore (SG)

(*) Notice: Subject to any disclaimer, the term of this patent is extended or adjusted under 35 U.S.C. 154(b) by 188 days.

(21) Appl. No.: 13/807,474

(22) PCT Filed: Jun. 30, 2011

(86) PCT No.: PCT/SG2011/000230
§ 371 (c)(1),
(2), (4) Date: Dec. 28, 2012

(87) PCT Pub. No.: WO2012/002912
PCT Pub. Date: Jan. 5, 2012

(65) Prior Publication Data
US 2013/0102805 A1 Apr. 25, 2013

Related U.S. Application Data

(60) Provisional application No. 61/398,803, filed on Jun. 30, 2010.

(51) Int. Cl.
*C07F 19/00* (2006.01)
*C04B 35/64* (2006.01)
*C04B 35/01* (2006.01)
*C04B 35/482* (2006.01)
*C04B 35/50* (2006.01)
*C04B 35/515* (2006.01)
*C04B 38/00* (2006.01)
*C04B 111/00* (2006.01)

(52) U.S. Cl.
CPC .............. *C07F 19/00* (2013.01); *C04B 35/01* (2013.01); *C04B 35/482* (2013.01); *C04B 35/50* (2013.01); *C04B 35/515* (2013.01); *C04B 38/0041* (2013.01); *C04B 2111/0081* (2013.01); *C04B 2235/3206* (2013.01); *C04B 2235/3217* (2013.01); *C04B 2235/3225* (2013.01); *C04B 2235/3227* (2013.01); *C04B 2235/3229* (2013.01); *C04B 2235/3244* (2013.01); *C04B 2235/3246* (2013.01); *C04B 2235/3418* (2013.01); *C04B 2235/3826* (2013.01); *C04B 2235/386* (2013.01); *C04B 2235/3873* (2013.01); *C04B 35/64* (2013.01)

(58) Field of Classification Search
USPC ............................. 556/28; 501/1, 134; 264/44
See application file for complete search history.

(56) References Cited

U.S. PATENT DOCUMENTS

| | | |
|---|---|---|
| 6,576,579 B2 | 6/2003 | Merkel |
| 7,468,156 B2 | 12/2008 | Noguchi et al. |
| 2004/0051196 A1 | 3/2004 | Otsuka et al. |
| 2007/0033912 A1 | 2/2007 | Furukawa et al. |
| 2008/0207581 A1 | 8/2008 | Whiteford et al. |
| 2009/0208744 A1 | 8/2009 | Komura et al. |

OTHER PUBLICATIONS

Chevalier, "Fabrication of Porous Substrates: A Review of Processes Using Pore Forming Agents in the Biomaterial Field," *Journal of Pharmaceutical Sciences*, vol. 97, pp. 1135-1154 (2008).
Xinwei Chen and Liang Hong, "An In Situ Approach to Create Porous Ceramic Membrane: Polymerization of Acrylamide in a Confined Environment," J. Am. Ceram. Soc., 93[1] 96-103 (2010).
Arkas et al. "Organosilicon Dendritic Networks in Porous Ceramics for Water Purification" *Chem. Mater.* 17(13): 3439-3444 (2005).
Bart Van der Bruggen et al. "A Review of Pressure-Driven Membrane Processes in Wastewater Treatment and Drinking Water Production" *Environmental Progress*, 22(1): 46-56 (Apr. 2003).
M. A. Keane "Ceramics for Catalysis" *Journal of Materials Science*, 38: 4661-4675 (2003).
Oomman K. Varghese et al. "Highly ordered nanoporous alumina films: Effect of pore size and uniformity on sensing performance" *J. Mater. Res.*, 17(5): 1162-1171 (May 2002).
Laxmidhar Besra and Meilin Liu "A review on fundamentals and applications of electrophoretic deposition (EPD)" *Progress in Materials Science*, 52: 1-61 (2007).
M. T. Ravanchi et al. "Application of membrane separation processes in petrochemical industry: a review" *Desalination*, 235: 199-244 (2009).
Stephen W. Sofie "Fabrication of Functionally Graded and Aligned Porosity in Thin Ceramic Substrates with the Novel Freeze-Tape-Casting Process" *J. Am. Ceram. Soc.*, 90(7): 2024-2031 (2007).
Eugene A. Olevsky "Theory of sintering: from discrete to continuum" *Materials Science and Engineering*, R23: 41-100 (1998).
T. Moritz and H.J. Richter "Ice-mould freeze casting of porous ceramic components" *Journal of the European Ceramic Society*, 27: 4595-4601 (2007).
A. Kritikaki and A. Tsetsekou "Fabrication of porous alumina ceramics from powder mixtures with sol-gel derived nanometer alumina: Effect of mixing method" *Journal of the European Ceramic Society*, 29: 1603-1611 (2009).
Takahashi et al. "Opportunities of porous ceramics fabricated by gelcasting in mitigating environmental issues" *Journal of the European Ceramic Society*, 29: 823-828 (2009).
Prabhakaran et al. "Preparation of a Porous Cermet SOFC Anode Substrate by Gelcasting of NiO-YSZ Powders" *J. Am. Ceram. Soc.*, 90(2): 622-625 (2007).

(Continued)

*Primary Examiner* — Porfirio Nazario Gonzalez
(74) *Attorney, Agent, or Firm* — Cesari and McKenna, LLP

(57) ABSTRACT

A porous ceramic matrix contains a plurality of ceramic particles adhered to each other, and a plurality of channels defined by surfaces of neighboring ceramic particles, the channels each having an average diameter of 0.5-2.5 μm. Preferred ceramics also have a porosity of 25.0-40.0%, a Darcy's Permeability of $1.57\text{-}34.8\times10^{-14}$ m$^2$, and a mechanical strength of 25-64 MPa. Also disclosed is a method of preparing such a porous ceramic matrix, comprising providing a pellet containing ceramic particles that are coated with a monomer, a catalyst, and a binder; polymerizing the monomer in the solid state by heating, then carbonizing and sintering the pellet.

23 Claims, No Drawings

(56) References Cited

OTHER PUBLICATIONS

Moreira et al. "Permeability of ceramic foams to compressible and incompressible flow" *Journal of the European Ceramic Society*, 24: 3209-3218 (2004).

Gregorova et al. "Porosity and pore space characteristics of starch-processed porous ceramics" *J Mater. Sci.*, 41: 6119-6122 (2006).

Zivcova et al. "Thermal conductivity of porous alumina ceramics prepared using starch as a pore-forming agent" *Journal of the European Ceramic Society*, 29: 347-353 (2009).

Peter J. Burchill "Chemical Characterization of Kevlar-49" *Journal of Materials Science*, 13: 2275-2276 (1978).

Lopez-Gandara et al. "YSZ-Based Oxygen Sensors and the Use of Nanomaterials: A Review from Classical Models to Current Trends" *Journal of Sensors*, pp. 1-15 (2009).

R.J. Gorte and J.M. Vohs "Nanostructured anodes for solid oxide fuel cells" *Current Opinion in Colloid & Interface Science*, 14: 236-244 (2009).

Wang et al. "Substrate Effect on the Melting Temperature of Thin Polyethylene Films" *Physical Review Letters*, 96: pp. 028303-1 to 028303-4 (2006).

D.A. Mooney and J.M.D. MacElroy "Theoretical Studies of the Structure and Dynamics of Semicrystalline PPTA/Water Vapor Interfaces" *Langmuir*, 13: 1173-1181 (1997).

Hayashi et al. "Thermal Expansion coefficient of yttria stabilized zirconia for various yttria contents" *Solid State Ionics*, 176: 613-619 (2005).

Gibson et al. "Sinterability of commercial 8 mol % yttria-stabilized zirconia powders and the effect of sintered density on the ionic conductivity" *Journal of Materials Science*, 33: 4297-4305 (1998).

Eugene Ryshkewitch "Compression Strength of Porous Sintered Alumina and Zirconia" *Journal of the American Ceramic Society*, 36(2): 65-68 (Feb. 1953).

Clasen et al. "How dilute are dilute solutions in extensional flows?" *J Rheol.*, 50(6): 849-881 (2006).

Nasir et al. "Preparation of PVDF/PMMA Blend Nanofibers by Electrospray Deposition: Effects of Blending Ratio and Humidity" *Polymer Journal*, 41(5): 402-406 (2009).

Freire et al. "Processability of PVDF/PMMA blends studied by torque rheometry" *Materials Science and Engineering C*, 29: 657-661 (2009).

Nicotera et al. "Investigation of ionic conduction and mechanical properties of PMMA-PVdF blend-based polymer electrolytes" *Solid State Ionics*, 177: 581-588 (2006).

N. Chen and L. Hong "Surface phase morphology and composition of the casting films of PVDF-PVP blend" *Polymer*, 43: 1429-1436 (2002).

Higashi et al. "Random copolyamides of terephthalic acid, $p$-penylenediamine and $p$-aminobenzoic acid soluble in $N$-methylpyrrolidone/$CaCl_2$," *Macromol. Rapid Commun.*2000, 21, 1044-1045.

Lyckfeldt et al. "Processing of Porous Ceramics by 'Starch Consolidation'" *Journal of the European Ceramic Society* 18 (1998) 131-140.

Liu et al. "Effects of CeO2 addition on the properties of cordierite-bonded porous SiC ceramics," *Journal of the European Ceramic Society*, vol. 29 (2009) 1795-1802. p. 1799.

Latella, et al. "Permeability and high temperature strength of porous mullite-alumina ceramics for hot gas filtration," *Journal of Materials Science*, vol. 41 (206), pp. 423-430.

Sepulveda et al. "Processing of Cellular Ceramics by Foaming and in situ Polymerisation of Organic Monomers," *Journal of the European Ceramic Society*, vol. 19 (1999), pp. 2059-2066.

_US 9,000,199 B2_

POROUS CERAMIC MATRIX

CROSS REFERENCE TO RELATED APPLICATION

This application is the National Stage of International Application No. PCT/SG2011/000230, filed Jun. 30, 2011, which claims the priority of U.S. Provisional application No. 61/398,803, filed Jun. 30, 2010. The contents of the aforementioned applications are incorporated herein in their entirety.

BACKGROUND OF THE INVENTION

Porous ceramic matrices have gained remarkable popularity in various industrial applications (e.g., catalysis support and water treatment) due to their thermal and chemical stability in severe environments, such as high temperatures, redox atmospheres, and corrosive liquids, as well as their mechanical reliability and durability.

Many techniques have been developed to prepare porous ceramic matrices. See Chevalier, _J. Pharm. Sci.,_ 97(3), 1135-1154, 2008. Among them, use of polymer pore-forming fillers remains a popular choice in ceramic processing, in view of their low costs and easy removal by thermal decomposition. However, self-coiling and aggregation tendency of polymer fillers could result in low permeability of the porous ceramic matrices prepared by this method, as the polymer fillers might fail to form a continuous phase. Such a problem can be resolved by increasing loadings of polymer fillers, but at the cost of mechanical properties of the ceramic matrices.

There is a need for preparing porous ceramic matrices with desired permeability and mechanical properties.

SUMMARY OF THE INVENTION

One aspect of this invention relates to a porous ceramic matrix.

The ceramic matrix of this invention contains a plurality of ceramic particles adhered to each other, and a plurality of channels defined by surfaces of neighboring ceramic particles, the channels each having a diameter of 0.5-2.5 µm. The matrix features a porosity of 25.0-40.0%, a Darcy's permeability of $1.57\text{-}34.8\times10^{-14}$ m$^2$ (e.g., $20\text{-}34.8\times10^{-14}$ m$^2$), and a mechanical strength of 25-64 MPa (e.g., 40-60 MPa). Optionally, the channels include narrow segments, each of which has a diameter smaller than 100 nm.

The ceramic particles can be made of yttria, zirconia, alumina, aluminosilicate, silica, ceria, gadolinium-doped-ceria, magnesia, nickel-doped magnesia, zinc oxide, boron nitride, silicon carbide, silicon nitride, yttria-stabilized zirconia, lanthanum oxide, alkaline earth metal-doped lanthanum oxides, or a combination thereof.

Another aspect of this invention relates to a method of preparing a porous ceramic matrix.

The method includes the following steps: (1) providing a ceramic pellet containing ceramic particles that are coated with a monomer, a catalyst, and a binder; (2) polymerizing the monomer in solid state by heating to form a polymer embedded in the ceramic pellets; (3) carbonizing the polymer, catalyst and binder at a temperature (e.g., 300-1000° C.) to generate a porous ceramic pellet; and (4) sintering the porous ceramic pellet at a temperature (e.g., 1000-1700° C.) to form a porous ceramic matrix. The monomer is 1-10% by weight, the catalyst is 1-5% by weight, and the binder is 1-20% by weight of the ceramic particles.

Examples of the monomer include, but are not limited to, acryl amide, terephthalic acid, p-phenylene diamine, p-hydroxybenzonic acid, 4,4'-oxydiphthalic anhydride, 4,4'-diaminodiphenyl ether, 3,3'-diamino benzidine, 4,6-diamino-1,3-benzene-diol dihydrochloride, 2,5-diamino-1,4-benzenedithiol dihydrochloride, 3,3'-diamino benzidine, or a combination thereof.

The catalyst used in the polymerizing step can be any catalyst that is suitable for thermal polymerization in solid state. It includes, but is not limited to, (1) an initiator for free radical polymerization (e.g., ammonium peroxodisulfate, benzoyl peroxide, and a combination thereof), and (2) a Lewis acid-based catalyst for step polymerization (e.g., lithium chloride, beryllium chloride, hydrofluoric acid, boron trifluoride, aluminum chloride, and a combination thereof).

Examples of the binder include, but are not limited to, polyvinyl butyral, polyvinyl alcohol, poly(ethene oxide), acrylic polymers, cellulose derivatives (e.g., cellulose ethers, methylcellulose, hydroxypropylmethyl cellulose, and hydroxyethyl cellulose), or a combination thereof.

The polymer, having a rigid chain structure, is preferred in this invention. Examples of the polymer include, but are not limited to, polyacrylamide, poly(p-phenyleneterephthalamide), poly(p-hydroxybenzate), polyester, polyimide, polybenzimidazole, polybenzoxazole, polybenzthiazole, an aromatic ladder polymer, or a combination thereof. It is preferred that the polymer has an average degree of polymerization ranging from 5 to 100.

Also within the scope of this invention are porous ceramic matrices prepared by the above-described method.

The details of one or more examples of the invention are set forth in the description below. Other features, objects, and advantages of the invention will be apparent from the detailed description of the examples and also from the appending claims.

DETAILED DESCRIPTION OF THE INVENTION

This invention is based in part on an unexpected discovery that a new preparation method leads to a porous ceramic matrix that has excellent permeability and reliable mechanical properties.

The porous ceramic matrix includes (1) a plurality of ceramic particles adhered to each other, and (2) a plurality of extensively interconnected channels. The channels are defined by surfaces of neighboring ceramic particles. In one embodiment, all or a significant number of the channels contain one or more narrow segments (i.e., throat-like pores), each of which has a diameter smaller than 100 nm. This unique channel structure results in an unusual capability of a ceramic matrix to induce a shear thinning effect when a pressure-driven dilute polymer solution passes through the matrix. The aforementioned throat-like pores contribute to stretching solvated polymer molecules, making the flow less viscous.

Below are exemplary procedures for preparing porous ceramic matrices of this invention in which ceramic particles are made of yttria-stabilized zirconia (YSZ).

A monomer, e.g., terephthalic acid and p-phenylene diamine, is dissolved in a solvent (e.g., ethanol) to form a solution, before YSZ particles are introduced to the solution and stirred to form a suspension. The solvent is then evaporated, yielding homogenous monomer-coated YSZ particles. If the monomer cannot be dissolved, but has a low melting point, it can be heated, together with YSZ particles, and upon melting, coat the YSZ particles.

Next, a binder (e.g., polyvinyl butyral) is dissolved in another solvent (e.g., 2-butanone and toluene) to form a binder solution. It can also include, in the binder solution, a non-ionic surfactant (e.g., Span-80), a deflocculating agent (e.g., fish oil), and/or a plasticizer (e.g., dibutyl phthalate). To this binder solution is then added a catalyst (e.g., lithium chloride in ethanol), followed by addition of the monomer-coated YSZ particles. The resultant slurry is homogenized by stirring before the solvent is evaporated to yield dried solids, which are ground and sieved into fine powder. The fine powder is then placed in a die set and pressed to obtain a ceramic pellet, in which the monomer is typically 1-10% by weight, the catalyst 1-5% by weight, and the binder 1-20% by weight of the ceramic particles.

A ceramic pellet can also be formed by different addition sequences as described in X. Chen et al., *J. Am. Ceram. Soc.*, 93[1] 96-103, 2010.

Subsequently, the ceramic pellet is heated to polymerize the monomer in solid state in an inert atmosphere (e.g., argon). Depending on the monomer, the heating temperature varies. As shown in the examples below, extension of the polymerization duration (e.g., 12 or 24 hrs) can yield in channels narrow segments that have a diameter smaller than 0.01 µm.

The polymers thus obtained, as well as the organic additives (e.g., the binder and the catalyst), are burned out in a furnace by slowly increasing the temperature (e.g., 300-1000° C.), leaving behind channels between the ceramic particles, the channels being formed of connected pores. To ensure complete removal of carbon, the temperature can be maintained for a period of time (e.g., 400° C., 4 hours). During the burning out process, air can be fed into the furnace to improve the combustion rate. Finally, the temperature is increased to a sintering temperature (e.g. 1000-1700° C.) to form a porous ceramic matrix.

In the method of this invention, pore-forming polymers are prepared in-situ in a compact environment (i.e., a ceramic pellet). This pore-forming method has three advantages: First, a small-sized monomer can achieve a higher degree of uniformity in a ceramic pellet than its large-molecular-weight counterpart. Second, shorter molecular chains are generated in this constrained polymerization environment, thereby minimizing the effects of random entanglement and agglomeration, which are thermodynamic tendencies of longer polymer chains. Third, polymer chains formed during in-situ solid state thermal polymerization can develop space occupancy through chain penetration and association, leaving behind interconnecting pore channels and more open pores after they are removed eventually. Thus-obtained porous ceramic matrices have excellent permeability and rupture resistivity compared to those made from conventional methods.

The porous ceramic matrix of this invention can be used in water treatment, catalysis support, gas sensors, solid oxide cells, and biomedical devices.

Without further elaboration, it is believed that one skilled in the art can, based on the disclosure herein, utilize the present invention to its fullest extent. The following specific examples are, therefore, to be construed as merely descriptive, and not limitative of the remainder of the disclosure in any way whatsoever. All publications cited herein are incorporated by reference.

Preparation of a Porous YSZ Matrix with Monomers
(i) Coating YSZ Particles with Monomers An equimolar mixture of terephthalic acid (TA, 98%, Sigma-Aldrich) and p-phenylene diamine (p-PDA, Sigma-Aldrich) were introduced into 30 mL of ethanol. The resulting solid-liquid mixture was mechanically stirred for 30 minutes. To the resultant suspension where only fine particles of p-PDA were left, yttria (8 mol %) fully stabilized zirconia (YSZ, median particle diameter of 0.5-1.0 µm, specific surface area of 15 m$^2$/g, Stanford Material Corporation, USA) powder with a ratio of 100/5 by weight to the two monomers was introduced into the suspension and stirred for another 30 minutes. The solvent was then allowed to evaporate naturally, resulting in a homogenous powder mixture of the TA-coated YSZ particles and p-PDA. The mixture was then subjected to a heat treatment at 150° C. for 30 minutes to melt p-PDA, which then covered the surfaces of the YSZ particles and merged with the previously coated TA layer.

(ii) Fabrication of YSZ Pellets and In-Situ Solid State Polymerization

A polymer binder solution was prepared by dissolving 1.5 g of polyvinyl butyral (PVB, Butvia-79, Solutia, USA) in 14 mL of a mixed solvent, containing equal amounts of 2-butanone and toluene. Other ingredients required to facilitate the ceramic fabrication process include: non-ionic surfactant—Span-80 (Sorbitan Monostearate, Sigma-Aldrich, USA), deflocculating agent—Manhattan fish oil (Sigma-Aldrich) and plasticizer—dibutyl phthalate (Acros Organic, USA). Lithium chloride (ACS reagent, Sigma-Aldrich) (16.7 wt % of the monomers) was then dissolved in 5 mL of ethanol and the homogenous solution was added to the polymer binder solution. After stirring for 15 minutes, the monomer-coated YSZ particles (15 g) were slowly added into this viscous solution. The resultant slurry was homogenized by mechanical blending and the solvent was allowed to gradually evaporate, leaving behind relatively large chunks of dried solids. These solids were then ground using a mortar and sieved into a fine powder using 325 mesh (opening: 45 µm). The resultant powder consisted of components by weight as follows: YSZ (100), monomers+catalyst (5+1), a PVB binder (10 or 5), fish oil+surfactant+plasticizer (0.6+0.6+1.2). An amount of the fine powder (5 g) was then placed in a cylindrical die set. A pellet (ø=13 mm) was pressed using a pressure of 5×10$^7$ Pa. The pressure was applied for 10 mins before the pellet was discharged from the die set. The loading of the two monomers in the green disc is about 4.2 wt %. The ceramic pellet was then transferred into a furnace and subjected to a temperature of 140° C. under the purging of argon (30 L/hr) to conduct the condensation polymerization of TA and p-PDA. The duration was varied from 6 hrs to 24 hrs. In addition, a control sample using starch (BDH Chemicals) as a pore former was prepared to serve as a benchmark.

(iii) Fabrication of the Sintered Porous YSZ Matrix Via Carbonization and Incineration Steps The ceramic pellets prepared from the previous step were heated at a rate of 0.5° C./min till 400° C. It was then maintained for 4 hours at this temperature to pyrolyze the PVB binder and the other organic additives. The temperature was increased at a rate of 2.5° C./min and set to dwell at 1000° C. and 1350° C. for 1 and 4 hrs, respectively. Finally, the furnace was then allowed to cool down to 1000° C. at a rate of 2.5° C./min and maintained for 1 hr before proceeding to room temperature at a rate of 2.5° C./min. The sintered matrices with different preparation history are listed in Table 1.

TABLE 1

| a | Porosity | Darcy's Permeability, $k_1$ (×10$^{-14}$ m$^2$) | Improvement in Permeability[b] | Mean Strength (MPa) |
|---|---|---|---|---|
| S$_5$-PPTA_1_6 | 34.7 ± 1.1 | 1.62 ± 0.05 | 50% | 40 ± 5 |
| S$_5$-PPTA_1_12 | 35.4 ± 0.6 | 1.62 ± 0.06 | 50% | 48 ± 4 |

TABLE 1-continued

| a | Porosity | Darcy's Permeability, $k_1$ (×10$^{-14}$ m$^2$) | Improvement in Permeability[b] | Mean Strength (MPa) |
|---|---|---|---|---|
| $S_5$-PPTA_1_24 | 35.4 ± 0.6 | 1.89 ± 0.06 | 75% | 47 ± 5 |
| $S_{10}$-PPTA_1_6 | 37.4 ± 0.6 | 1.89 ± 0.06 | 40% | 29 ± 5 |
| $S_{10}$-PPTA_1_12 | 32.6 ± 2.4 | 2.16 ± 0.05 | 60% | 42 ± 14 |
| $S_{10}$-PTA_1_24 | 29.5 ± 1.0 | 2.43 ± 0.04 | 80% | 50 ± 14 |
| $C_5$-PDA/TA_1_0 | 35.9 ± 1.6 | 1.35 ± 0.05 | 25% | 39 ± 5 |
| $C_{10}$-PDA/TA_1_0 | 36.4 ± 1.0 | 1.35 ± 0.02 | 0% | 29 ± 5 |
| $C_5$-Starch | 30.6 ± 1.6 | 1.08 ± 0.03 | — | 28 ± 6 |
| $C_{10}$-Starch | 34.0 ± 0.5 | 1.35 ± 0.02 | — | 25 ± 9 | a: The subscript of S represents the weight percentage of the PVB binder in the green pellet. The first digit of the suffix indicates the weight percentage of catalyst (LiCl) and the second shows the duration of the condensation polymerization in the green pellet in hours. The weight basis is based on 100 wt % of ceramic powder.
b: Comparison was carried out by using $C_5$-Starch and $C_{10}$-Starch as basis for 5 wt % and 10 wt % of a polymer binder used respectively.

Characterizations
(i) Thermal Analysis

The polymerization extent of TA and p-PDA in a green ceramic body was examined by the thermal analysis on a differential scanning calorimetry (DSC, Modulated DSC 2920, TA Instrument, Newcastle, Del.) in a nitrogen atmosphere. In this analysis, the thermal history of the sample was removed by heating it from 25° C. to 110° C. at 20° C./min and holding it for a minute. The thermal scan was then conducted from 0° C. to 520° C. at 10° C./min.

Two control samples, i.e., pellets $C_5$-PDA/TA_1_0 and $C_{10}$-PDA/TA_1_0 were tested first. As indicated by the labels in the footnote of Table 1, these two samples were not subjected to polymerization condition and differed from each other in the amount of PVB used. They displayed two sets of melting points of TA and p-PDA, which depart from the melting points in their pure forms (TA: 402° C., p-PDA: 147° C.). Such variation in the melting point, in particular, TA, can be attributed to different extents of mixing of the monomers with the processing additives. For the sample $S_5$-PPTA_1_6, which was subjected to polymerization at 140° C. for 6 h, the disappearance of the melting point of TA indicates that TA molecules were either polymerized or dissolved in the processing additive layer.

With the extension of the polymerization time to 12 and 24 h, the polymer (PPTA) formed in the green pellet can be identified from the corresponding DSC diagrams, in which the melting peak of the PPTA crystallites emerged in the temperature range of ca. 260° C. to 280° C. This range is much lower than the known melting point of crystalline PPTA phase at 450° C., indicating the existence of crystallite.

(ii) Surface Morphologies of YSZ Pellets after Polymerization

The microstructures of the YSZ pellets, i.e., $S_{10}$-PPTA_1_t (t=12 or 24), after the polymerization process and the sintering step, were observed on a field emission scanning electron microscope (FESEM, JEOL JSM-6700F, Tokyo, Japan).

The "surface extrusion" phenomenon of polymer was observed. Micro needles of PPTA were found in the surface layer due to the lower pressure of the surface compared to the bulk, which leads to the squeezing out of these polymers from the layer beneath the surface.

(iii) Thermogravimetric Analysis

The weight loss of a green YSZ pellet after polymerization was monitored using a thermogravimetric analysis (TGA, DTG-60AH, Shimadzu, Singapore) to understand the removal of the combustibles such as PPTA during the calcination process. The analysis was conducted in air and the temperature was scanned from 30° C. to 1000° C. with a heating rate of 10° C./min.

A comparison of TGA diagram of the YSZ matrix, $S_{10}$-PPTA_1_24, with that of the control, $C_{10}$-Starch, shows a clear divergence of mass elimination in the temperature range from 350° C. to 1000° C. The TGA diagrams show that the processing additives and most of the starch has been totally removed before 500° C., while the decomposition of PPTA completes at about 950° C. with gradual weight lost from 450° C. This was also confirmed via the micrographs of the pellets that contained carbonized PPTA after being calcined at 600° C. and 800° C. These micrographs showed that carbonized rods of PPTA were embedded with the YSZ particles and the necking phenomenon was still rare at its initial stage even at 800° C. The examination on the microstructures of the two sintered bulk phases indicated that the control contains coagulations that result in a more congested bulk phase, whereas $S_{10}$-PPTA_1_24 matrix exhibited a well connected porous microstructure. By combining the results of TGA and electron microscopy observation, it was concluded a dual role of PPTA as a pore former: it creates interconnecting pore channels via its shape and size exclusion inside the green body; the carbonization residue of it holds the particle packing through restricting inter-particle motions until the interaction between YSZ particles become sufficiently strong due to thermal expansion and preliminary necking.

(iii) Porosity Analysis

The porosity of a sintered ceramic matrix was measured by the Archimedes method. This technique requires the measurements of the dry mass of a porous specimen, $m_1$ and the mass of the specimen when fully impregnated with water, $m_2$. The density of the water, $\rho_w$ and YSZ, $\rho_{YSZ}$ is taken to be 1 g/cm$^3$ and 6.1 g/cm$^3$ respectively. The porosity of the specimen $\phi$ is then calculated using the formula:

$$\phi = \frac{\frac{m_2 - m_1}{\rho_w}}{\frac{m_2 - m_1}{\rho_w} + \frac{m_1}{\rho_{YSZ}}} \qquad \text{Eqn. 1}$$

The mean pore radius and the pore size distribution of a sintered pellet were measured by the mercury porosimetry (Micrometrics AutoPore III, Norcross, Ga.).

Similar to a study described in X. Chen et al., *J. Am. Ceram. Soc.*, 93[1] 96-103, 2010, a template of the pore channels of the sintered pellet was obtained. The sintered matrices were soaked in a solution of chloroform (4.925 g) and Span-80 (0.075 g) for 3 hrs. After drying, the matrices were then transferred to another solution containing styrene (5 g), divinylbenzene (a crosslinker, 0.5 g) and benzoyl peroxide (an initiator, 0.2 g) to soak for another 3 hrs. The Span-80 modified pore-wall facilitated the entrance of the monomer feed stream. The matrices after impregnation were transferred into deionized water to seal the monomers inside the matrices. The entrapped monomers were then polymerized at 50° C. for a day before subjected to pyrolysis for 2 hrs at 600° C. in an argon atmosphere. The carbon filaments formed were then observed under FESEM.

The porosity values of the sintered YSZ matrices are listed in Table 1.

According to the pore size distribution curves of the sintered $S_{10}$-PPTA_1_t matrices, the control $C_{10}$-Starch shows smaller pore sizes and wider pore size distribution than $S_{10}$-PPTA_1_t pellets. This trend was also observed for $C_5$-Starch and $S_5$-PPTA_1_t matrices. Another important observation is the presence of small pore sizes in the range of less than 0.01 μm for $S_{10}$-PPTA_1_12 and $S_{10}$-PPTA_1_

24. These throat-like features occur in those locations where the carbonization residue between particles were lastly removed at temperatures near 950° C. as they were thin and in minority. The technique of portraying pore channels by the carbon template exhibited sub-micron carbon filaments with slim branches in the cross-sectional of $S_{10}$-PPTA_1_24. This FESEM observation was in accord with the mercury intrusion examination and the argument that better interconnecting channels were formed by in-situ polymer generation technique.

(iv) Modulus of Rupture

The modulus of rupture (MOR) of the YSZ matrices at room temperature was characterized by a 3-point bending test, which was conducted on a micro-tester (Instron 550 MicroTester, Instron Singapore Pte Ltd., Singapore). Rectangular test specimens were made by cutting the circular pellets with a diamond saw and the sides were polished using fine sand paper. These test specimens were placed in a fixture with a span length of 20 mm to carry out the bending experiment. The crosshead speed of the micro-tester was set at 0.05 cm min$^{-1}$. The MOR (S) for a rectangular test specimen can be calculated using the following formula:

$$S = \frac{3*P*L}{2*b*d^2} \quad \text{Eqn. 2}$$

where P is the fracture strength (Pa), L is the span length of the fixture (m), d is the thickness of the specimen (m) and b is the width (m).

The mechanical strength values of the $S_{10}$ and $S_5$ series and the controls are listed in Table 1. It could be observed that the strength levels of the $S_{10}$ and $S_5$ series are generally greater than the controls.

(v) Fluid Flow Behavior

The gas permeability of a sintered YSZ matrix was measured using the module designed in a previous study described in X. W. Chen et al., *J. Am. Ceram. Soc.*, 93[1], 96-103, 2010. Similarly, the edge of the matrix was sealed with an aluminum sticker to prevent any leakage of gas. The surface area of the matrix exposed to air was 3.14 cm$^2$. Compressed air was selected to measure the permeability of all the sintered matrices. The permeability results are shown in Table 1.

To explore the interconnectivity of the pore channels, an experiment was designed to measure rheological responses of a dilute polymer solution when it passes through different YSZ matrices. 0.2 g of poly(methyl methacrylate) (PMMA, Paraloid A-11, Rohm and Haas, $M_w$ 125 000) and 0.2 g of poly(vinylidene fluoride) (PVDF, Sigma-Aldrich, $M_w$ 534 000) were each dissolved in 50 ml n-butyl acetate (0.45 wt % polymer solution) separately. The two solutions were stirred for 12 hrs to assure a homogeneous bulk phase before their shear viscosity ($\eta$) values at steady state of 200 rpm were measured by viscometer (Brookfield DV-II+Pro Viscometer, USA). These two solutions were then mixed by mechanical means for another 1 hr, after which their shear viscosity was measured again. The resultant dilute polymer binary solution was then passed though the fabricated YSZ matrix and the shear viscosity of permeate was noted.

Initially, PVDF and PMMA solutions in butyl acetate were prepared and both recorded the same viscosity of 0.75 cP. After mixing, the viscosity of the mixture increased to 1.00 cP, indicating the affinity nature of the two polymers. The shear viscosity of the binary solution after passing through a porous matrix is listed in Table 2. An obvious increase in viscosity of the polymer solution was observed in the case when it was extruded through those matrices that showed high air permeability values, e.g., $S_5$-PPTA_1_t (t=24) and $S_{10}$-PPTA_1_t (t=12 and 24). The dynamic sizes of both polymers in butyl acetate, measured by dynamic light scattering at room temperature, fall in the range of 1-3 μm, which are approximately 200-300 times larger than the throat-like pores (<0.01 μm, based on the largest size of the submicron pores found in $S_{10}$-PPTA_1_12 and $S_{10}$-PPTA_1_24). Due to the restricted flow path pattern, the polymers opened up their coils and assumed a more linear form, which favors chain interaction between the adjacent polymer chains either in the throat-like pores or after extrusion from these pores. Meanwhile, adsorption of the polymers on the pore walls resulted in no-slip zone, which in-turn facilitated decoiling of the polymers. Thus, the increase in viscosity of the extruded polymer solution is a direct evidence of improved mixing since it causes inter-chain physical association.

TABLE 2

| Shear Viscosity of PMMA/PVDF blend (cP) | | | |
|---|---|---|---|
| | Before filtration | After filtration | % Change |
| $S_5$-PPTA_1_6 | 1.00 | 1.00 | 0 |
| $S_5$-PPTA_1_12 | 1.00 | 1.00 | 0 |
| $S_5$-PPTA_1_24 | 1.00 | 1.13 | 0.13 |
| $S_{10}$-PPTA_1_6 | 1.00 | 1.00 | 0 |
| $S_{10}$-PPTA_1_12 | 1.00 | 1.25 | 0.25 |
| $S_{10}$-PPTA_1_24 | 1.00 | 1.25 | 0.25 |
| $C_{10}$-PPTA_1_0 | 1.00 | 1.00 | 0 |
| $C_5$-Starch | 1.00 | 1.00 | 0 |
| $C_{10}$-Starch | 1.00 | 1.00 | 0 |

However, for those of the $S_{10}$ and $S_5$ pellets with shorter or nil polymerization time, the extrudate did not show any increase in viscosity. This implies that interconnectivity and less tortuosity traits are beneficial to the mixing process over a long range of pore channel extension. On the contrary, blockages along the pore channels give rise to interruption of extrudate surface and therefore gliding of the liquid layer attached to pore-wall, which undermines shear thinning effect. Coupled with the discussion in previous sections, this in-situ pore generation technique makes smaller pores far more accessible, especially those that are less than 0.01 μm. It is proposed that these throats exert combing action on polymer chains on top of the effect of no-slip layer. Finally, as expected, the controls show no effects on the viscosity of extrudate.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other examples are also within the claims.

What is claimed is:

1. A porous ceramic matrix, the matrix comprising a plurality of ceramic particles adhered to each other, and a plurality of channels defined by surfaces of neighboring ceramic particles, the channels each having an average diameter of 0.5-2.5 μm, wherein the matrix features a porosity of 25.0-40.0%, a Darcy's permeability of $1.57\text{-}34.8\times10^{-14}$ m$^2$, and a mechanical strength of 25-64 MPa, wherein the channels include narrow segments, each of the narrow segments having a diameter smaller than 100 nm.

2. The porous ceramic matrix of claim 1, wherein the ceramic particles are made of yttria, zirconia, alumina, aluminosilicate, silica, ceria, gadolinium-doped-ceria, magnesia, nickel-doped magnesia, zinc oxide, boron nitride, silicon carbide, silicon nitride, yttria-stabilized zirconia, lanthanum oxide, alkaline earth metal-doped lanthanum oxides, or a combination thereof.

3. The porous ceramic matrix of claim 2, wherein the ceramic particles are made of yttria-stabilized zirconia.

4. The porous ceramic matrix of claim 3, wherein the channels include narrow segments, each of the narrow segments having a diameter smaller than 100 nm.

5. The porous ceramic matrix of claim 1, wherein the Darcy's permeability is $20\text{-}34.8\times10^{-14}$ m$^2$ and the mechanical strength is 40-60 MPa.

6. The porous ceramic matrix of claim 5, wherein the channels include narrow segments, each of the narrow segments having a diameter smaller than 100 nm.

7. The porous ceramic matrix of claim 5, wherein the ceramic particles are made of yttria, zirconia, alumina, silica, ceria, gadolinium-doped-ceria, magnesia, nickel-doped magnesia, boron nitride, silicon carbide, silicon nitride, yttria-stabilized zirconia, lanthanum oxide, alkaline earth metal-doped lanthanum oxides, or a combination thereof.

8. The porous ceramic matrix of claim 7, wherein the ceramic particles are made of yttria-stabilized zirconia.

9. The porous ceramic matrix of claim 8, wherein at least one of the channels has one or more narrow segments each having a diameter smaller than 100 nm.

10. A method for preparing a porous ceramic matrix, the method comprising:
providing a ceramic pellet containing ceramic particles that are coated with a monomer, a catalyst, and a binder;
polymerizing the monomer in solid state by heating to form a polymer embedded in the ceramic pellets;
carbonizing the polymer, catalyst and binder to generate a porous ceramic pellet; and
sintering the porous ceramic pellet to form a porous ceramic matrix;
wherein the monomer is 1-10% by weight, the catalyst is 1-5% by weight, and the binder is 1-20% by weight of the ceramic particles.

11. The method of claim 10, wherein the ceramic particles are made of yttria, zirconia, alumina, silica, ceria, gadolinium-doped-ceria, magnesia, nickel-doped magnesia, boron nitride, silicon carbide, silicon nitride, yttria-stabilized zirconia, lanthanum oxide, alkaline earth metal-doped lanthanum oxides, or a combination thereof.

12. The method of claim 11, wherein the ceramic particles are made of yttria-stabilized zirconia.

13. The method of claim 10, wherein the monomer is acryl amide, terephthalic acid, p-phenylene diamine, p-hydroxybenzonic acid, 4,4'-oxydiphthalic anhydride, 4,4'-diaminodiphenyl ether, 3,3'-diamino benzidine, 4,6-diamino-1,3-benzene-diol dihydrochloride, 2,5-diamino-1,4-benzenedithiol dihydrochloride, 3,3'-diamino benzidine, or a combination thereof.

14. The method of claim 10, wherein the catalyst is ammonium peroxodisulfate, benzoyl peroxide, lithium chloride, beryllium chloride, hydrofluoric acid, boron trifluoride, aluminum chloride, or a combination thereof.

15. The method of claim 10, wherein the binder is polyvinyl butyral, polyvinyl alcohol, poly(ethene oxide), acrylic polymers, cellulose ethers, methylcellulose, hydroxypropylmethyl cellulose, hydroxyethyl cellulose, or a combination thereof.

16. The method of claim 10, wherein the polymer has an average degree of polymerization ranging from 5 to 100.

17. The method of claim 16, wherein the polymer is polyacrylamide, poly(p-phenyleneterephthalamide), poly(p-hydroxybenzate), polyester, polyimide, polybenzimidazole, polybenzoxazole, polybenzthiazole, an aromatic ladder polymer, or a combination thereof.

18. The method of claim 17, wherein the polymer is poly (p-phenyleneterephthal amide).

19. The method of claim 18, wherein the ceramic particles are made of yttria-stabilized zirconia.

20. The method of claim 10, wherein the carbonizing step is performed at 300-1000° C.

21. The method of claim 10, wherein the sintering step is performed at 1000-1700° C.

22. A porous ceramic matrix prepared by the method of claim 10.

23. A porous ceramic matrix prepared by the method of claim 19.

* * * * *